US011041840B2

(12) United States Patent
Do Quang et al.

(10) Patent No.: US 11,041,840 B2
(45) Date of Patent: Jun. 22, 2021

(54) PROCESS FOR MONITORING THE CONCENTRATION OF BACTERIA IN A WATER DISTRIBUTION NETWORK

(71) Applicant: SUEZ GROUPE, Paris la Défense (FR)

(72) Inventors: Zdravka Do Quang, Bailly (FR);
Sophie Courtois, Le Pecq (FR);
Guillaume Cussonneau, Paris (FR);
Gilles Fay, Paris (FR)

(73) Assignee: SUEZ GROUPE, Paris la Défense (FR)

( * ) Notice: Subject to any disclaimer, the term of this patent is extended or adjusted under 35 U.S.C. 154(b) by 102 days.

(21) Appl. No.: 16/309,872

(22) PCT Filed: May 17, 2017

(86) PCT No.: PCT/EP2017/061798
§ 371 (c)(1),
(2) Date: Dec. 13, 2018

(87) PCT Pub. No.: WO2018/001627
PCT Pub. Date: Jan. 4, 2018

(65) Prior Publication Data
US 2019/0250138 A1 Aug. 15, 2019

(30) Foreign Application Priority Data
Jun. 30, 2016 (FR) ...................... 1656225

(51) Int. Cl.
*G01N 33/18* (2006.01)
*C12Q 1/04* (2006.01)
*C02F 1/00* (2006.01)

(52) U.S. Cl.
CPC ............... *G01N 33/18* (2013.01); *C12Q 1/04* (2013.01); *G01N 33/1826* (2013.01);
(Continued)

(58) Field of Classification Search
None
See application file for complete search history.

(56) References Cited

U.S. PATENT DOCUMENTS 10,266,441 B2 * 4/2019 Lee .................. C02F 1/4676
2004/0020862 A1 2/2004 Baca et al.
(Continued)

OTHER PUBLICATIONS

Bakker, et al., "Monitoring water supply systems for anomaly detection and response", IWC International Water Conference: New Developments in IT & Water, Nov. 4, 2012.
(Continued)

*Primary Examiner* — David W Berke-Schlessel
(74) *Attorney, Agent, or Firm* — BakerHostetler

(57) ABSTRACT

A process for monitoring the concentration of bacteria in the water of a water distribution network, wherein the process includes the following steps: measuring the concentration of bacteria in the water by means of a first sensor positioned at a first location in the water distribution network, determining a variable instantaneous value of the expected concentration of bacteria in the water at the first location as a function of a parameter characteristic of the water, comparing the concentration of bacteria in the water measured by the first sensor to the variable instantaneous value, corrective action acting on the concentration of bacteria in the water if the concentration of bacteria in the water measured by the first sensor exeeds the variable instantaneous value. A device for monitoring the concentration of bacteria in the water of a water distribution network is also provided.

7 Claims, 3 Drawing Sheets

(52) U.S. Cl.
CPC .......... *C02F 1/008* (2013.01); *C02F 2209/36* (2013.01); *C02F 2307/14* (2013.01); *Y02A 20/20* (2018.01)

(56) References Cited

U.S. PATENT DOCUMENTS

| | | |
|---|---|---|
| 2004/0158432 A1 | 8/2004 | King et al. |
| 2005/0009192 A1 | 1/2005 | Page |
| 2006/0031040 A1* | 2/2006 | Wolfe ..................... C02F 1/008 702/184 |
| 2008/0293042 A1* | 11/2008 | Cooper ................. G01N 33/18 435/5 |
| 2010/0066547 A1* | 3/2010 | Chowdhury ....... G01N 15/0205 340/603 |

OTHER PUBLICATIONS

Ramírez-Castillo, et al., "Waterborne Pathogens: Detection Methods and Challenges", Pathogens, vol. 4(2), pp. 307-334, May 21, 2015.
Database Compendex [Online] Engineering Information, Inc., New York, NY, US; aout 2010 (Aug. 2010), Fisher S: "Free software tool to monitor water supply", XP055351285, Database accession No. E20103813246460 abrege & Pollution Engineering Aug. 2010 BNP Media USA, vol. 42, No. 8, aout 2010 (Aug. 2010).

* cited by examiner

PROCESS FOR MONITORING THE CONCENTRATION OF BACTERIA IN A WATER DISTRIBUTION NETWORK

CROSS-REFERENCE TO RELATED APPLICATIONS

This application is a National Stage of International patent application PCT/EP2017/061798, filed on May 17, 2017, which claims priority to foreign French patent application No. FR 1656225, filed on Jun. 30, 2016, the disclosures of which are incorporated by reference in their entirety.

FIELD OF THE INVENTION

The invention pertains to the field of online measurement of bacteriological quality in water distribution circuits and relates to a process for monitoring the concentration of bacteria in a water distribution circuit. The invention also relates to a device for monitoring the concentration of bacteria in a water distribution network. The invention may be used to monitor any type of water, be this water in a cooling network, natural water, environmental water or treated water.

BACKGROUND

Tap water undergoes continuous health monitoring, with the aim of guaranteeing health safety, i.e. the absence of pathogenic microorganisms. In terms of pathogenic microorganisms, mention may be made of bacteria, viruses and parasites. In this application only bacteria will be addressed but, obviously, it is understood that the invention applies in a similar fashion to monitoring the concentration of any microorganism, whether pathogenic or non-pathogenic.

The presence of bacteria in drinking water is most often due to a deterioration in the quality of the water resource, poor protection or a lack of maintenance of catchment infrastructures, a failure of the disinfection treatment, or contamination of the water during its conveyance or storage in the network.

Methods for seeking pathogens in water are time-consuming and complex, so the bacteriological quality of water is generally assessed on the basis of control microorganisms. Finding these microorganisms in water is thus evidence that pathogens might be present. Similarly, other microorganisms encompassing all microorganisms that are able to grow on a non-specific nutrient substrate under standard conditions are an indication of the overall burden of microorganisms in water.

These indicators, however, derive from culture-based detection methods. They require one-off sampling, laboratory analyses, and incubation times ranging from several hours to several days. Yet it is possible to count only viable, microorganisms amenable to culture, but these represent just a small proportion of the microorganisms present in water. Furthermore, instances of microbiological contamination are likely to occur sporadically over short periods of time and they may be very diverse in origin. Mention may be made, in particular, of a one-off treatment failure, a resuspension of sediments or biofilm detachment, leaks, a backflow of water, or even vandalism. This type of method is thus unreliable.

There thus appears to be a need to continuously monitor water microflora and to carry out measurements in real time using, for example, an analysis frequency of under 30 minutes.

Online measurement methods exist. The most advanced methods for monitoring water quality use multiparameter probes that make it possible to measure a large number of physico-chemical parameters. These methods are poor indicators of microbiological contamination of a liquid. Of these methods, only turbidity can be used as an overall indicator of microbiological quality, but it can also be adversely affected by the presence of a variety of suspended matter, such as sludge, clay, fine particles of organic and inorganic matter, and other soluble colored organic compounds.

Optical methods, and in particular the counting of particles by means of pattern recognition from images or by diffusion or occultation of a light beam, may be used to study concentration in terms of particles and/or bacteria or microorganisms. Thus, fluorescence measurements are also possible. There are therefore means for measuring continuously and online, by delivering a signal in terms of the number of particles or bacteria per unit volume of liquid sample analyzed. The signal obtained is then compared to a pre-established threshold value, and an alarm may be generated if the signal obtained exceeds the pre-established threshold value. Using the same principle, the alarm may be generated as a function of the evolution of the signal beyond a pre-established rate of increase of the signal. Pre-establishment of this threshold value or rate of increase of the signal is based on empiricism or interpretation of the base line, which requires a prior continuous series of measurements of the total bacterial concentration over a time window of one to several weeks. The threshold value is thus very often imprecise and does not necessarily correspond to the operating conditions of the distribution network. The signal obtained, for example, from the number of total bacteria is poorly exploited. Indeed, if an increase in the number of total bacteria is observed, this signal is not processed so that it is possible to differentiate between an increase owing to a normal change in conditions, for example after a change in water flow in the water distribution network, or an abnormal change, for example a water treatment defect.

SUMMARY OF THE INVENTION

The aim of the invention is to palliate the aforesaid problems, entirely or in part, by proposing a process for monitoring the concentration of bacteria in a water distribution network on the basis of a threshold value that adapts to the various available data on the distribution network. This process makes it possible to enhance operational use of the data derived from monitoring bacteriology for water networks. Processing of the data thus enables a network operator to better visualize network behavior and to instigate corrective and preventive actions with greater efficiency.

To that end, the subject of the invention is a process for monitoring the concentration of bacteria in the water of a water distribution network, characterized in that it comprises the following steps:

measuring the concentration of bacteria in the water by means of a first sensor positioned at a first location in the water distribution network, determining a variable instantaneous value of the expected concentration of bacteria in the water at the first location as a function of a parameter characteristic of the water, comparing the concentration of bacteria in the water measured by the first sensor to the variable instantaneous value.

According to one embodiment, the monitoring process according to the invention may comprise a corrective action acting on the concentration of bacteria in the water if the concentration of bacteria in the water measured by the first sensor exceeds the variable instantaneous value.

According to one embodiment, the monitoring process according to the invention comprises a step of saving the concentration of bacteria in the water measured by the first sensor in a database such as to constitute a log of the concentrations of bacteria in the water measured by the first sensor, and the parameter characteristic of the water is determined as a function of the log of the concentrations of bacteria in the water measured by the first sensor.

According to another embodiment, the monitoring process according to the invention comprises a step of measuring a plurality of characteristics of the water, and the parameter characteristic of the water is determined as a function of at least one of the plurality of measured characteristics of the water.

According to one embodiment, the monitoring process according to the invention further comprises a step of measuring the concentration of bacteria in the water measured by a second sensor positioned at a second location in the water distribution network, and the parameter characteristic of the water is determined as a function of the concentration of bacteria in the water measured by the second sensor.

Advantageously, the corrective action comprises a step of injecting a product capable of countering the development of the bacteria.

Advantageously, the monitoring process according to the invention further comprises a step of slaving the corrective action as a function of a difference between the concentration of bacteria in the water measured by the first sensor and the variable instantaneous value.

The invention also relates to a device for monitoring the concentration of bacteria in the water of a water distribution network, comprising:
- a first sensor, positioned at a first location in the water distribution network, intended to measure a concentration of bacteria in the water at the first location,
- a calculator intended to determine a variable instantaneous value of the expected concentration of bacteria in the water at the first location as a function of a parameter characteristic of the water,
- a comparator intended to compare the concentration of bacteria in the water measured by the first sensor to the variable instantaneous value.

According to one embodiment of the invention, the monitoring device comprises a correction unit intended to act on the concentration of bacteria in the water if the concentration of bacteria in the water measured by the first sensor exceeds the variable instantaneous value.

According to one embodiment of the invention, the monitoring device comprises a database intended to save the concentration of bacteria in the water measured by the first sensor such as to constitute a log of the concentrations of bacteria in the water measured by the first sensor, and the calculator is designed to determine the parameter characteristic of the water as a function of the log of the concentrations of bacteria in the water measured by the first sensor.

According to another embodiment of the invention, the monitoring device comprises a device for measuring a plurality of characteristics of the water, and the calculator is designed to determine the parameter characteristic of the water as a function of at least one of the plurality of measured characteristics of the water.

According to another embodiment of the invention, the monitoring device comprises a second sensor, positioned at a second location in the water distribution network, intended to measure a concentration of bacteria in the water at the second location, and the calculator is designed to determine the parameter characteristic of the water as a function of the concentration of bacteria in the water measured by the second sensor.

Advantageously, the correction unit comprises a device for injecting a product capable of countering the development of the bacteria.

Advantageously, the monitoring device comprises a slaving of the correction unit as a function of a difference between the concentration of bacteria in the water measured by the first sensor and the variable instantaneous value.

BRIEF DESCRIPTION OF THE DRAWINGS

The invention will be better understood and further advantages will become apparent upon reading the detailed description of one embodiment given by way of example, which description is illustrated by the attached drawing in which.

For the sake of clarity, the same elements will bear the same references in the various figures.

DETAILED DESCRIPTION

In the description, the invention is described on the basis of a wastewater example. The invention is applicable, however, to any other liquid that contains particles.

Figure 1:
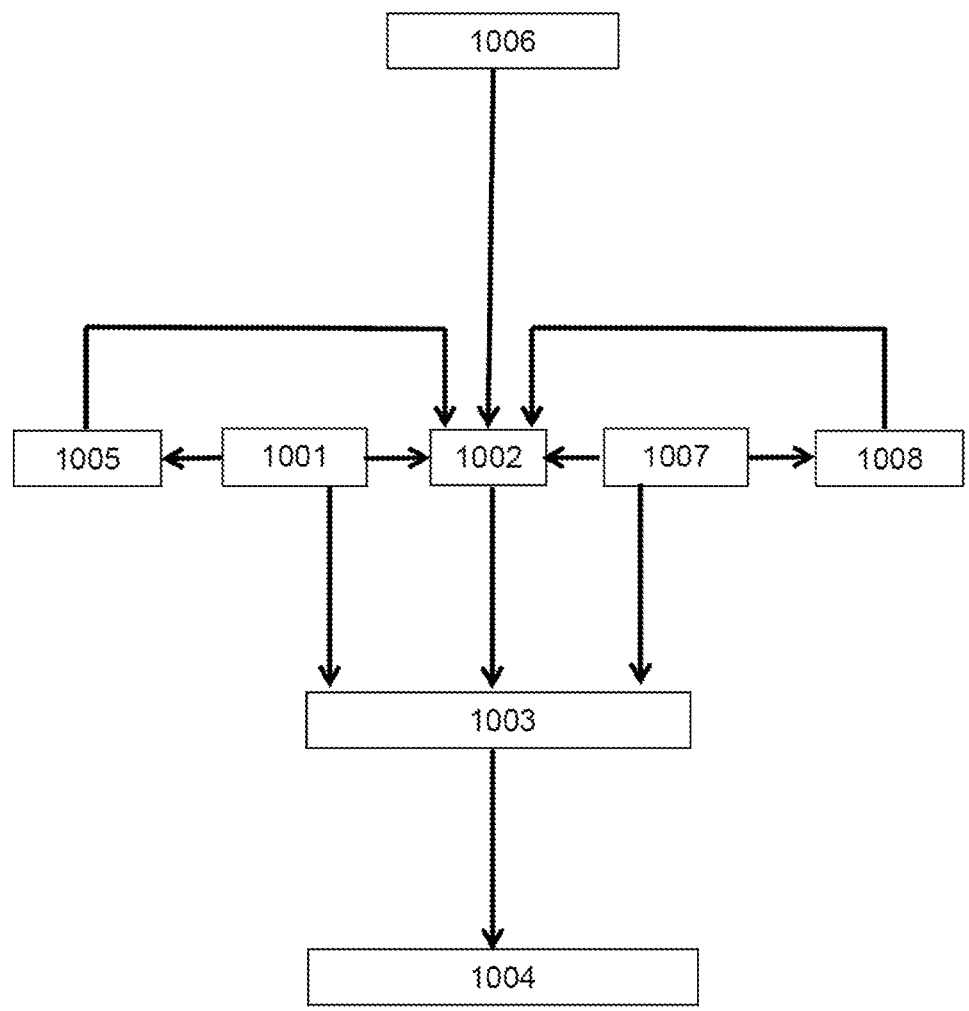
FIG. 1 schematically shows the steps in a process for monitoring the concentration of bacteria in the water of a water distribution network according to the invention, FIG. 2 schematically shows an embodiment of a device for monitoring the concentration of bacteria in the water of a water distribution network according to the invention, FIG. 3 schematically shows another embodiment of a device for monitoring the concentration of bacteria in the water of a water distribution network according to the invention.

FIG. 1 schematically shows the steps in a process for monitoring the concentration of bacteria in the water of a water distribution network according to the invention. The process for monitoring the concentration of bacteria in the water of a water distribution network comprises a step 1001 of measuring the concentration of bacteria in the water by means of a first sensor positioned at a first location in the water distribution network. The monitoring process according to the invention comprises a step 1002 of determining a variable instantaneous value of the expected concentration of bacteria in the water at the first location as a function of a parameter characteristic of the water. As explained above, it is possible to pre-establish a threshold value that the concentration of bacteria in the water should not exceed empirically. It has, however, been shown that this value does not necessarily take account of the evolution of the system overall. Indeed, it is perfectly possible that, at a given instant, the concentration of bacteria measured in the water will exceed an empirical threshold value on account of, for example, the normal evolution of external conditions. Determining a variable instantaneous value as a function of a parameter characteristic of the water makes it possible to take account of normal or abnormal changes in the water distribution network. The parameter characteristic of the water is an evolving parameter taken into account by online measurement of the concentration of the bacteria and also other parameters, as discussed below in the description. In other words, the variable instantaneous value is not a fixed value. This value evolves as the process according to the invention progresses. In other words, the variable instantaneous value of the expected concentration of bacteria corresponds to a threshold that takes account of the surrounding conditions of the water distribution network. Different water qualities, corresponding to different sources, different treatment processes, and different hydrological regimes may thus be taken into account without generating false alarms. Evolutions in the level of concentration of bacteria owing to phenomena having an impact on other parameters but not requiring any intervention can thus be distinguished on the basis of a threshold that reflects the expected level. This threshold is the variable instantaneous value. This variable instantaneous value is thus fully suited to monitoring the concentration of bacteria in water.

A step 1003 of comparing the concentration of bacteria in the water measured by the first sensor to the variable instantaneous value then takes place. It is also noted that there may be a comparison between the concentration of bacteria in the water measured by the first sensor and the variable instantaneous value or else the variable instantaneous value to which a difference is added, in order to incorporate a degree of tolerance into the figure that constitutes the threshold.

It may be noted that step 1002 of determining the variable instantaneous value of the concentration of bacteria expected at the first location may take place before, during or just after the measuring step 1001. In any event, step 1002 has to take place before step 1003 of comparing the concentration of bacteria in the water measured by the first sensor to the variable instantaneous value.

The variable instantaneous value is dependent on surrounding conditions, and a single variable instantaneous value is determined before comparison step 1003, which means that a new variable instantaneous value is determined before each comparison. In other words, as the variable instantaneous value evolves and is regularly updated there is no need to save this value in a universal database. Simple storage of the log suffices. The monitoring process according to the invention is thus easier to manage.

The characteristic parameter comprises the surrounding conditions of the water network and the log of the measurements taken. The characteristic parameter is therefore a vector of values deriving from these two components: current status of the characteristics of the water and the measurement log.

It is, furthermore, important to stress that step 1001 of measuring the concentration of bacteria in the water by means of the first sensor positioned at the first location in the water distribution network takes place in situ, not in the laboratory. The invention thus make it possible continuously to monitor the microflora of the water and to take measurements in real time.

Lastly, the monitoring process according to the invention may comprise a step 1004 of corrective action acting on the concentration of bacteria in the water if the concentration of bacteria in the water measured by the first sensor exceeds the variable instantaneous value. When the monitoring process comprises the step 1004 of corrective action, the corrective action generally takes place if the concentration of bacteria in the water measured by the first sensor significantly exceeds the variable instantaneous value. It is, here, a question of the measured concentration of bacteria in comparison to the variable instantaneous value. The significance of this overshoot reflects the consideration of a number of time steps greater than 1 with an overshoot in a specific window of time. This makes it possible to avoid instigating the corrective action on the basis of a single overshoot, which may correspond to an aberrant value, thereby reducing the number of false alarms. Using the same principle, the invention also applies to the increase in the concentration of bacteria in the water measured by the first sensor, which would then be compared to a variable instantaneous value as a function of a characteristic parameter of the water taking account of the evolution in the concentration of bacteria.

Comparison step 1003 may be carried out at a predefined frequency, for example every 10 minutes, or over a time interval and/or by taking account of a series of measurements of concentration of bacteria.

According to one embodiment of the invention, the monitoring process may comprise a step 1005 of saving the concentration of bacteria in the water measured in step 1001 by means of the first sensor in a database such as to compile a log of the concentrations of bacteria in the water measured by the first sensor. The parameter characteristic of the water that allows the variable instantaneous value to be determined can thus be determined as a function of the log of concentrations of bacteria in the water measured by the first sensor.

According to one embodiment, the characteristic parameter is represented by the estimated parameters of a statistical distribution of observed values of bacterial concentrations comprising, for example, an empirical mean and standard deviation. According to another embodiment, the characteristic parameter is represented by a discrete class representing a water quality observed for the bacteriological measurement.

According to another embodiment of the invention, the monitoring process may comprise a step 1006 of measuring a plurality of characteristics of the water, and the parameter characteristic of the water is determined as a function of at least one of the plurality of measured characteristics of the water. According to one embodiment, the characteristic parameter can thus be expressed by the estimated parameters of the statistical distributions of observed values of the various physico-chemical and bacteriological characteristics measured. According to another embodiment, the characteristic parameter may be represented by a discrete class representing a water quality observed for the bacteriological measurement.

Among water characteristics, mention may be made, for example and in a non-exhaustive manner, of pressure, flow rate, water pH, water temperature, water conductivity, the chlorine content of the water, water turbidity, the total organic carbon content of the water, or the dissolved oxygen concentration in the water. These characteristics may be measured online or in the laboratory. The value taken into consideration for each of the characteristics may be a minimum of the value, a maximum of the value, a mean or a quantile. The parameter characteristic of the water may be determined as a function of a single characteristic of the water, for example temperature or chlorine content, or of a plurality of characteristics, for example water temperature, chlorine content and pH. Also, one or more of these characteristics of the water may be an indicator on an evolution in the concentration of bacteria in the water. This is why it is important for it (them) to be taken into account in the determination of the parameter characteristic of the water in order to determine an instantaneous value, which is thus variable because it can change in value as a function of a change in value of the water parameter(s) beyond which an alarm may be instigated if the measured concentration of bacteria exceeds this instantaneous value thus determined.

It may be noted that determination of the variable instantaneous value may be based on the other parameters, but not solely so; it is necessary to have at least a few values of concentrations of bacteria in order to determine the base level or levels.

According to another embodiment of the invention, the monitoring process may further comprise a step 1007 of measuring the concentration of bacteria in the water by means of a second sensor positioned at a second location in the water distribution network, and the parameter characteristic of the water is determined as a function of the concentration of bacteria in the water measured by the second sensor. Step 1007 offers two major advantages. If the second sensor is positioned close to the first sensor in one and the same pipe of the water distribution network, with no branching between the two sensors, the concentrations of bacteria measured by the two sensors must be substantially the same. If the concentrations measured by the two sensors differ too much, this may be a sign that at least one of the two sensors is defective. In such a case, step 1007 allows verification of correct operation of the bacterial concentration sensors. If the second sensor is positioned at a distance from the first sensor, either in one and the same pipe or remotely in the water distribution network, or even in another pipe branched off the pipe of the first sensor, the second sensor gives a concentration of bacteria measured at a second location. This information on concentration at another location in the network may be used to calculate the parameter characteristic of the water with a view to making the value of the expected concentration of bacteria at the first location more precise for a given status of the distribution network at this moment.

Using the same principle, and in a similar fashion, the monitoring process may further comprise a step of measuring the concentration of bacteria in the water by means of a third sensor positioned at a third location in the water distribution network. The same rationale applies in the case of a plurality of other sensors.

Moreover, the monitoring process may comprise a step 1008 of saving the concentration of bacteria in the water measured in step 1007 by means of the second sensor in a database such as to compile a log of the concentrations of bacteria in the water measured by the second sensor. The parameter characteristic of the water that allows the variable instantaneous value to be determined can thus be determined as a function of the log of concentrations of bacteria in the water measured by the second sensor also.

More precisely, the parameter characteristic of the water that allows the variable instantaneous value to be determined may thus be determined as a function not only of the log of the concentrations of bacteria in the water measured by the first and second sensors, but also of the concentrations of bacteria in the water measured at the first and second locations at this instant.

Advantageously, the parameter characteristic of the water that allows the variable instantaneous value to be determined may thus be determined as a function of the log of the concentrations of bacteria in the water measured by the first and second sensors, as a function of the concentrations of bacteria in the water measured at the first and second locations at this instant, and also as a function of at least one of the plurality of measured characteristics of the water. This means that the variable instantaneous value, which is the value at which the concentration of bacteria measured by the first sensor is compared and which is decisive in terms of triggering the alarm signal if the measured concentration is too high relative to what it is supposed to be, adapts to the different available data on the distribution network and allows the characteristics specific to each type of water to be taken into account.

It may be noted that the invention applies in a similar fashion to a plurality of different sensors in one and the same water pipe and/or other locations in the water distribution network, and also in regard to saving the measured concentrations in order to compile the log of resulting measured concentrations. It is thus possible to determine the variable instantaneous value of the concentration of bacteria expected at a location as a function, inter alia, of the concentration of bacteria measured at a plurality of other locations in the network. This gives a variable instantaneous value that fully corresponds to the status of the water distribution network as a whole.

Advantageously, the corrective action in step 1004 comprises a step of injecting a product capable of countering the development of the bacteria. The corrective action generally takes the form of the injection of a disinfectant solution, for example chlorine or another biocide, into the distribution network. According to another embodiment, the corrective action in step 1004 comprises a purge of that part of the network that is affected by the overshoot in the variable instantaneous value.

Advantageously, the monitoring process according to the invention further comprises a step of slaving the corrective action as a function of a difference between the concentration of bacteria in the water measured by the first sensor and the variable instantaneous value. The difference gives an indication as to the discrepancy between the measured concentration and the concentration expected at the first location. Depending on how great this discrepancy is, a greater or lesser amount of product is injected. The slaving step of the corrective action allows the amount of product, for example chlorine, injected into the network to be adapted. Once the chlorine has been injected, a further measurement of the concentration of bacteria is carried out by the first sensor, another difference is calculated and, depending on the difference obtained, the amount of chlorine to be injected is adapted. If the measured concentration of bacteria is still too high relative to what it is supposed to be, the amount of chlorine injected may be increased or kept constant until the first sensor shows a decrease in the concentration of bacteria measured at the first location. If the measured concentration of bacteria is below the variable instantaneous value, the injection of chlorine is halted.

The monitoring process according to the invention thus allows monitoring of the concentration of bacteria in a water network in an evolutive, adaptive way, as a function of the status of the network as a whole and while taking account of variations in allied parameters, such as characteristics of the water and/or the log of concentrations at one or more other locations in the water distribution network.

Figure 2:
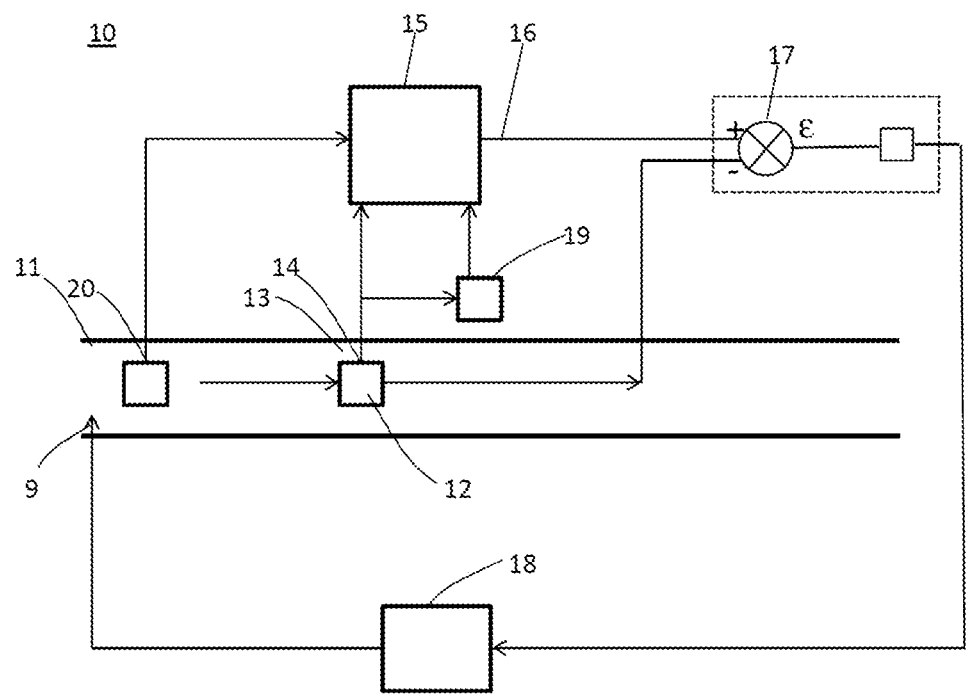

FIG. 2 schematically shows an embodiment of a device 10 for monitoring the concentration of bacteria in the water of a water distribution network according to the invention. The device 10 for monitoring the concentration of bacteria in the water of a water distribution network 11 may be used to implement the process as described in FIG. 1. The device 10 comprises a first sensor 12, positioned at a first location 13 in the water distribution network 11, intended to measure a concentration 14 of bacteria in the water at the first location 13. The device 10 comprises a calculator 15 intended to determine a variable instantaneous value 16 of the expected concentration of bacteria in the water at the first location 13 as a function of a parameter characteristic of the water. The device 10 comprises a comparator 17 intended to compare the concentration 14 of bacteria in the water measured by the first sensor 12 to the variable instantaneous value 16. The device 10 comprises a correction unit 18 intended to act on the concentration of bacteria in the water if the concentration 14 of bacteria in the water measured by the first sensor 13 is greater than the variable instantaneous value 16.

According to one embodiment of the invention, the device 10 may comprise a database 19 intended to save the concentration 14 of bacteria in the water measured by the first sensor 12 such as to compile a log of the concentrations of bacteria in the water measured by the first sensor 12. The database 19 may be integrated into the calculator 15 or into the sensor 12 or onto a support outside of the calculator 15 and the sensor 12. The calculator 15 is thus designed to determine the parameter characteristic of the water as a function of the log of concentrations of bacteria in the water measured by the first sensor 12. For example, the parameter characteristic of the water may be calculated by the calculator 15 on the basis of the log of the concentrations of bacteria in the water measured by the first sensor 12. The parameter characteristic of the water makes it possible to determine the variable instantaneous value 16. By virtue of the database 19, it is possible to perform, over time, a series of measurements of the concentration 14 of bacteria, over one day, one week, one month, or more, at regular or irregular intervals. These measurements are saved in the database 19. In addition, it is then possible to establish, during normal operation of the water distribution network, a mean value of the concentration of bacteria at the first location and an amplitude of normal fluctuations about the mean value, or another definition of a normal fluctuation interval. It is thus possible to study the statistical distribution observed in the log such as to better determine the variable instantaneous value that corresponds to an expected value for the concentration of bacteria in the water at the first location. One example is to consider a variable instantaneous value described in terms of a Gaussian distribution and the parameter characteristic of the water as being a certain standard deviation number or another parametric probability distribution. Another example makes it possible to take account of the observed seasonality of the concentration of bacteria by separating the seasonal trend from the initial signal, with a view to determining an instantaneous value that also reflects this seasonality. Another example employs the techniques of chronological series of decomposition of the signal into different components having their own periodicity. Another example consists in using non-parametric or statistical learning methods to obtain an expression of the variable instantaneous value as a function of the parameter characteristic of the water.

The monitoring device 10 according to the invention may comprise a device 20 for measuring a plurality of characteristics of the water. As explained above, among water characteristics, mention may be made, for example and in a non-exhaustive manner, of pressure, water flow rate, water temperature, water pH, water conductivity, the chlorine content of the water, water turbidity, or the dissolved oxygen concentration in the water. These characteristics may be measured online by the device 20 or in the laboratory. The value taken into consideration for each of the characteristics may be a minimum of the value, a maximum of the value, a mean or a quantile. The calculator 15 is designed to determine the parameter characteristic of the water as a function of at least one among the plurality of measured characteristics of the water. In such a case, the parameter characteristic of the water makes it possible to take account of the evolution of the measured concentration 14 of bacteria deriving from normal operation of the network. In other words, if the water temperature rises it is highly probable that the measured concentration 14 of bacteria will likewise increase. This increase in the measured concentration 14 of bacteria is thus not the result of a malfunction in the distribution network and does not necessarily require the same corrective action as in the case of another event that has an impact on the concentration of bacteria. It is thus important to take this differentiation into account and to be able to arrange for the variable instantaneous value 16 to evolve as a function of the surrounding conditions of the network. The variable instantaneous value of the concentration of bacteria may thus be determined by using a predictive model based on different characteristic parameters. In particular, different predictive models are tested as part of a cross-validation procedure using available past data, especially on the basis of data obtained by saving the concentration of bacteria measured at the first location. The most pertinent model, i.e. the model that gives the most advantageous performance levels (precision, sensitivity to aberrant values, short calculation time, and so on), is then selected for the calculation of the variable instantaneous value. The predictive models tested include, especially, statistical learning algorithms, in particular random forests and decision trees, generalized linear models, and neural networks.

The correction unit 18 of the monitoring device 10 comprises a device 9 for injecting a product capable of countering the development of the bacteria. The correction unit 18 generally comprises a device for injecting a disinfectant solution, for example chlorine or another biocide, into the distribution network. Advantageously, the injector is positioned well upstream of the first sensor 12 such that the measurements taken by the first sensor 12 after the corrective action can take account of the results of the corrective action.

Advantageously, the monitoring device 10 comprises a slaving of the correction unit 18 as a function of a difference between the concentration 14 of bacteria in the water measured by the first sensor 12 and the variable instantaneous value 16. Depending on the difference between the measured concentration and the concentration expected at the first location 13, the correction unit 18 is able to adapt the amount of product to be injected. The slaving of the correction unit 18 allows the amount of product, for example chlorine, injected into the network to be adapted.

Once the chlorine has been injected, a further measurement of the concentration 14 of bacteria is carried out by the first sensor 12, another difference is calculated and, depending on the difference obtained, the amount of chlorine to be injected is adapted. If the measured concentration of bacteria is still too high relative to what it is supposed to be, the amount of chlorine injected may be increased or kept constant until the first sensor 12 shows a decrease in the concentration of bacteria measured at the first location 13. If the measured concentration 14 of bacteria is below the variable instantaneous value 16, the injection of chlorine is halted. Slaving of this type allows reliable, precise adjustment of the concentration of bacteria in the distribution network.

Figure 3:
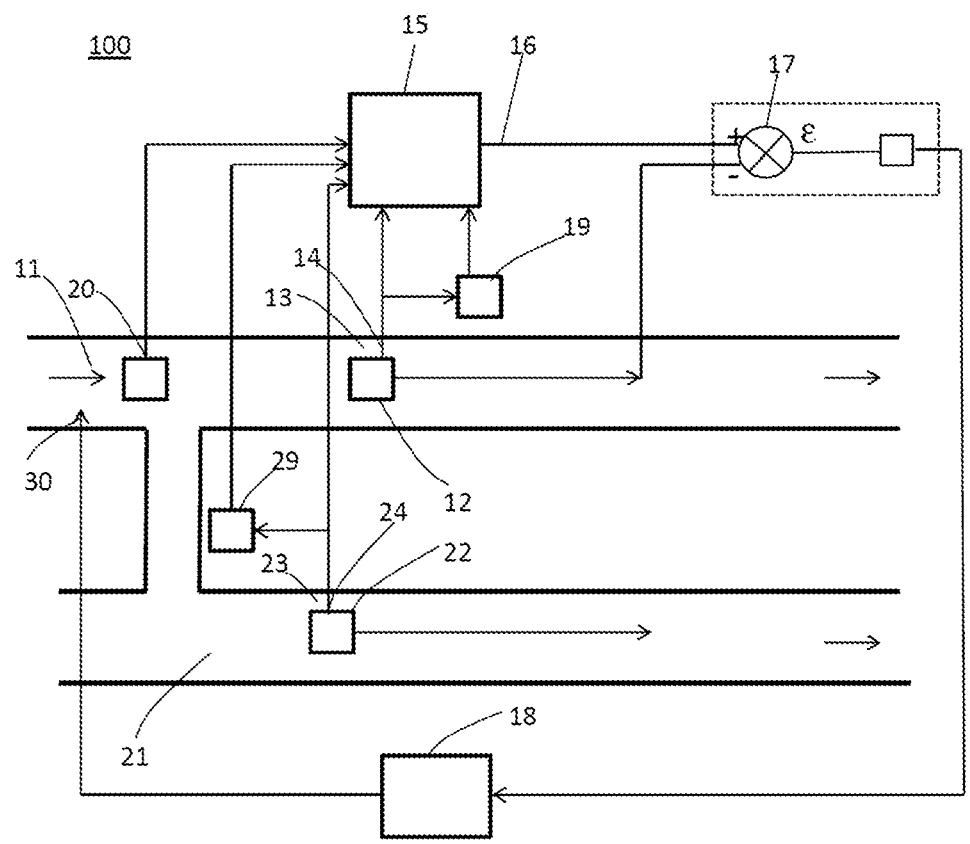

FIG. 3 schematically shows another embodiment of a device 100 for monitoring the concentration of bacteria in the water of a water distribution network according to the invention. The device 100 for monitoring the concentration of bacteria in the water of a water distribution network 11 may be used to implement the process as described in FIG. 1. All the elements of the device 100 in FIG. 3 are identical to the elements of the device 10 in FIG. 2. In the embodiment of FIG. 3, the device 100 is presented in the case of a water distribution network with two parallel pipes 11 and 21 that are branched together. In FIGS. 2 and 3 the water is flowing from left to right. In FIG. 3, the branching between the two pipes 11 and 21 lies upstream of the first sensor 12.

In this embodiment, the monitoring device 100 comprises a second sensor 22, positioned at a second location 23 in the water distribution network, intended to measure a concentration 24 of bacteria in the water at the second location 23. The calculator 15 is designed to determine the parameter characteristic of the water as a function of the concentration 24 of bacteria in the water measured by the second sensor 22. The second sensor 22 gives a concentration 24 of bacteria measured at a second location 23. This information on concentration at another location in the network may be used for the calculation of the parameter characteristic of the water, with a view to improving the precision of the value of the concentration of bacteria expected at the first location 13 in the case of a given status of the distribution network at this instant.

To facilitate reading and understanding, a device 100 with a first and a second sensor is described. Obviously, the invention also relates, in a similar manner, to a monitoring device having more than two sensors.

The estimation of the parameter characteristic of the water at the point of the first sensor may be improved by using historical data and an analysis of the linear or non-linear correlation between the parameters at the two locations. The variable instantaneous value of the concentration of bacteria may thus be determined by using a predictive model based on different characteristic parameters. In particular, different predictive models are tested as part of a cross-validation procedure using available past data, especially on the basis of data obtained by saving the concentration of bacteria measured at the first location. The most pertinent model, i.e. the model that gives the most advantageous performance levels (precision, sensitivity to aberrant values, short calculation time, and so on), is then selected for the calculation of the variable instantaneous value. The predictive models tested include, especially, statistical learning algorithms, in particular random forests and decision trees, generalized linear models, and neural networks.

Advantageously, the parameter characteristic of the water that allows the variable instantaneous value 16 to be determined may thus be determined as a function of the log of the concentrations 14, 24 of bacteria in the water measured by the first and second sensors 12, 22, as a function of the concentrations 14, 24 of bacteria in the water measured at the first and second locations 13, 23 at this instant, and also as a function of at least one of the plurality of measured characteristics of the water. This means that the variable instantaneous value 16, which is the value at which the concentration 14 of bacteria measured by the first sensor 12 is compared and which is decisive in terms of triggering the alarm signal if the measured concentration 14 is too high relative to what it is supposed to be, adapts to the different available data on the distribution network and allows the characteristics specific to each type of water to be taken into account.

As already explained, it may be noted that the invention applies in a similar fashion to a device with a plurality of different sensors in one and the same water pipe and/or at other locations in the water distribution network, and also in regard to saving the measured concentrations in order to compile the log of resulting measured concentrations. It is thus possible to determine the variable instantaneous value 16 of the concentration of bacteria expected at a location as a function, inter alia, of the concentration of bacteria measured at a plurality of other locations in the network. This gives a variable instantaneous value 16 that fully corresponds to the status of the distribution network as a whole.

Here, the invention relates to a calculator 15 that determines a variable instantaneous value 16 for a concentration of bacteria expected at a precise location, i.e. the first location 13. Obviously, the invention applies in a similar manner to another variable instantaneous value, or to a plurality of other variable instantaneous values, for another location, or for a plurality of other locations. The monitoring device may then employ a single calculator 15 designed to determine a plurality of variable instantaneous values or a plurality of calculators may be implemented to this end. Similarly, the device according to the invention may comprise a single correction unit, or a plurality of correction units, for acting on the concentrations of bacteria at different locations in the distribution network. Lastly, arranging the slaving of the correction units to allow action as a function of the differences between the measured concentrations of bacteria and the corresponding variable instantaneous values can be perfectly well envisaged within the context of the invention.

Furthermore, step 1002 in the monitoring process according to the invention may comprise a phase of learning that enables the calculator 15 to characterize normal situations as opposed to abnormal situations, on the basis, in particular, of the log of measured concentrations and any other available information. The learning phase may be repeated periodically in order to update the data-processing model. Therefore, the calculator 15 may be designed to perform a learning phase such as to be able to characterize normal situations as opposed to abnormal situations, on the basis of the log of measured concentrations and any other available information.

Thus, the process according to the invention and the device according to the invention make it possible to improve the operational use of the data deriving from monitoring bacteriology for water distribution networks. Processing of the data thus enables a network operator to better visualize network behavior and to instigate corrective and preventive actions with greater efficiency.

The invention may be applied to the monitoring of any type of water, for example cooling network water, natural water, environmental water, process water, or the recycling of wastewater. The first sensor 12 has been described as being positioned at the first location 13, but it may be bypassed with the medium where the water to be monitored is in circulation. In this application, the concentration measurements are explained for the case of bacteria, but the invention applies similarly to a group of bacteria, a genus or a species of bacteria, which are also indicators of the microbiological quality of water.

The invention claimed is:

1. A process for treating the concentration of bacteria in the water of a water distribution network under surrounding conditions, wherein the process comprises the following steps:

measuring the concentration of bacteria in the water by means of a first sensor positioned at a first location in the water distribution network, measuring surrounding conditions;

determining a single variable instantaneous value of the expected concentration of bacteria in the water, corresponding to a threshold that takes account of the surrounding conditions of the water distribution network, at the first location as a function of a changing parameter characteristic, said parameter comprising physico-chemical and bacteriological characteristics of the water, said parameter taking account of the surrounding conditions of the water network, wherein the single variable instantaneous value is thus evolving when at least one of the physicochemical and bacteriological characteristics and the surrounding conditions evolves, and the single variable instantaneous value of the expected concentration of bacteria is determined with a predictive model using past data, comparing the concentration of bacteria in the water measured by the first sensor to the variable instantaneous value, and correcting the concentration of bacteria in the water if the concentration of bacteria in the water measured by the first sensor exceeds the variable instantaneous value.

2. The treating process as claimed in claim 1, further comprising saving the concentration of bacteria in the water measured by the first sensor in a database such as to constitute a log of the concentrations of bacteria in the water measured by the first sensor, and in that the parameter characteristic of the water is determined as a function of the log of the concentrations of bacteria in the water measured by the first sensor.

3. The treating process as claimed in claim 1, further comprising measuring a plurality of characteristics of the water, and in that the parameter characteristic of the water is determined as a function of at least one of the plurality of measured characteristics of the water.

4. The treating process as claimed in claim 1, further comprising measuring the concentration of bacteria in the water measured by a second sensor positioned at a second location in the water distribution network, and in that the parameter characteristic of the water is determined as a function of the concentration of bacteria in the water measured by the second sensor.

5. The treating process as claimed in claim 1, wherein correcting the concentration of bacteria comprises injecting a product capable of countering the development of bacteria.

6. The treating process as claimed in claim 1, further comprising slaving the correcting as a function of a difference between the concentration of bacteria in the water measure by the first sensor and the variable instantaneous value.

7. The treating process as claimed in claim 1, wherein the predictive model includes at least one of statistical learning algorithms, random forests, decision trees, generalized linear models, and neural networks.

* * * * *